United States Patent [19]

Lee et al.

[11] Patent Number: 4,927,922

[45] Date of Patent: May 22, 1990

[54] 7β-(SUBSTITUTED)AMINO-3-SUBSTITUTED CEPHALOSPORANIC ACIDS AND ESTERS

[75] Inventors: Ving J. Lee, Monsey; William V. Curran, Pearl River, both of N.Y.

[73] Assignee: American Cyanamid Company, Stamford, Conn.

[21] Appl. No.: 222,463

[22] Filed: Jul. 21, 1988

Related U.S. Application Data

[63] Continuation-in-part of Ser. No. 882,996, Jul. 8, 1986, abandoned.

[51] Int. Cl.$^5$ .................. C07D 501/16; A61K 31/545
[52] U.S. Cl. .................................... 540/227; 540/221
[58] Field of Search ..................... 516/201; 514/206; 540/227, 225, 226

[56] References Cited

U.S. PATENT DOCUMENTS 4,399,132  8/1983  Curran et al. .................. 540/227
4,692,519  9/1987  Naitor et al. .................. 540/222

Primary Examiner—Nicholas S. Rizzo
Attorney, Agent, or Firm—Alan M. Gordon

[57] ABSTRACT

7β-(Substituted) amino-3-substituted cephalosporanic acids, esters and salts, useful as anti-bacterial agents are described.

21 Claims, No Drawings

7β-(SUBSTITUTED)AMINO-3-SUBSTITUTED CEPHALOSPORANIC ACIDS AND ESTERS

This application is a continuation-in-part of Ser. No. 882,996, filed July 8, 1986, now abandoned.

SUMMARY OF THE INVENTION

This invention is concerned with compounds of the formula:

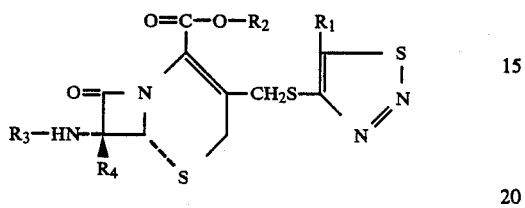

wherein $R_1$ is selected from the group consisting of hydrogen, alkyl($C_1$–$C_6$), polyfluorinated alkyl($C_1$–$C_6$), phenyl, multisubstituted phenyl wherein the substituents are selected from alkyl($C_1$–$C_6$), alkoxy($C_1$–$C_3$), chloro, fluoro and trifluoromethyl, naphthyl, thienyl, phenylthio, tetrahydropyranyl, benzyl, and —COOC$_2$H$_5$; $R_2$ is selected from the group consisting of hydrogen, diphenylmethyl, α-acyloxyalkyl, t-butyl, benzyl, 4-nitrobenzyl and 4-methoxybenzyl and pharmaceutically acceptable salts (sodium and potassium); and $R_3$ is selected from the group consisting of hydrogen,

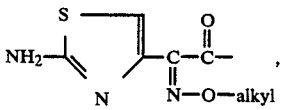

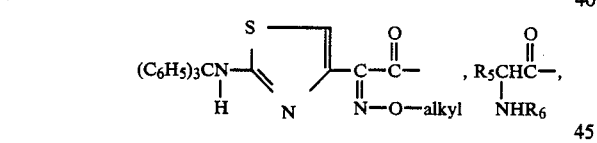

where $R_5$ is selected from the group consisting of phenyl, substituted phenyl, 2-thienyl, 2-furyl, trifluoromethylthiomethyl, 4-(2-aminothiazoyl), 5-(2-aminothiazoyl) and cyanomethylthiomethyl, and $R_6$ is selected from the group consisting of hydrogen, 4-alkyl(or aryl)-2,3-dioxopiperazine-1-carbonyl, ureido and carboxyamido, phenylacetyl, heterocyclic acetyl,

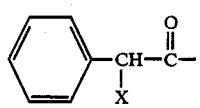

where X is selected from the group consisting of OH, SO$_3$H, COOH and tetrazolyl; and $R_4$ is selected from the group consisting of hydrogen, —O—alkyl, —S—alkyl and formamido.

DESCRIPTION OF THE INVENTION

The compounds of the present invention may be prepared according to the following reaction schemes.

Scheme A

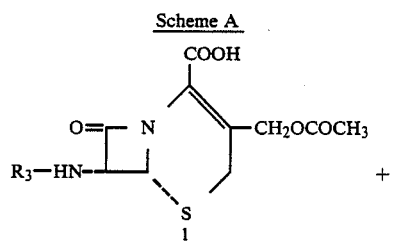

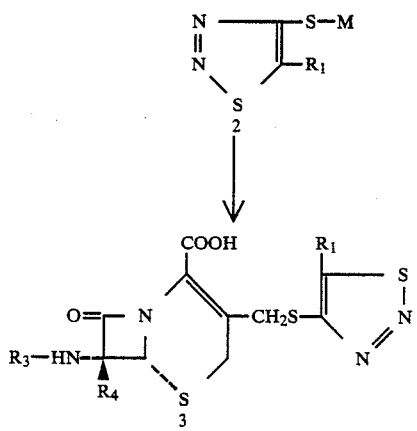

According to Scheme A, a cephalosporin 1, where $R_3$ is hydrogen, is reacted with a 1,2,3-thiadiazol-4-thiolate 2, where $R_1$ is as described above, with the proviso that $R_1$ cannot be hydrogen, methyl, propyl, isopropyl or n-butyl, and M is sodium or potassium in a solvent such as water at 50°–70° C. for 2–12 hours with pH adjustment to 6.0–7.0, giving the products 3.

Scheme B

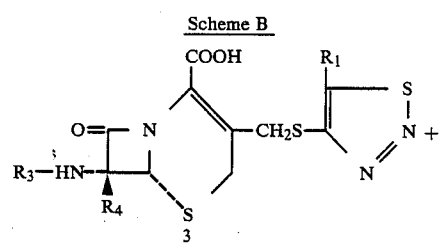

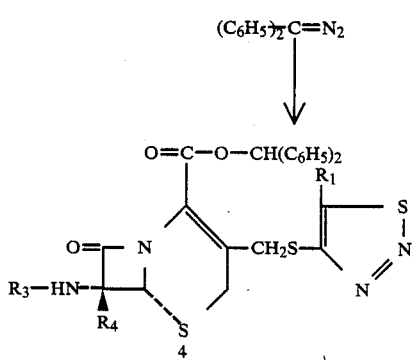

According to Scheme B, diphenylmethyl derivatives 4 are prepared by reaction of 3 with diphenyldiazomethane in acetonitrile.

Scheme C

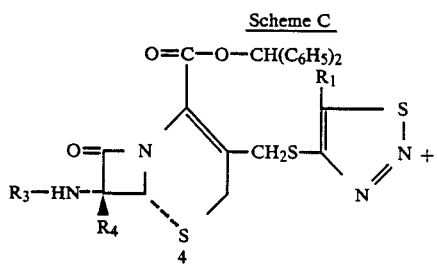

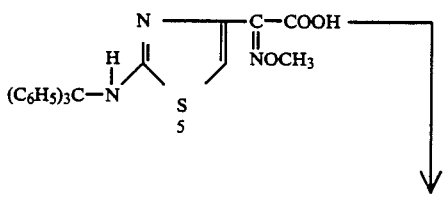

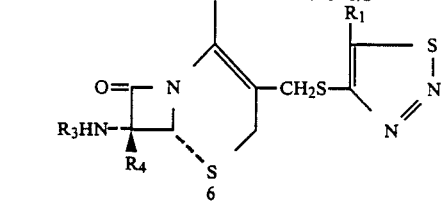

According to Scheme C, derivative 4, where $R_3$ is hydrogen is reacted with derivative 5 and 1-alkoxycarbonyl-2-alkoxy-1,2-dihydroquinolines in dichloromethane giving derivative 6, where $R_1$ is as described above and

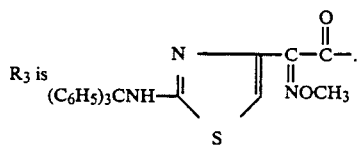

Scheme D

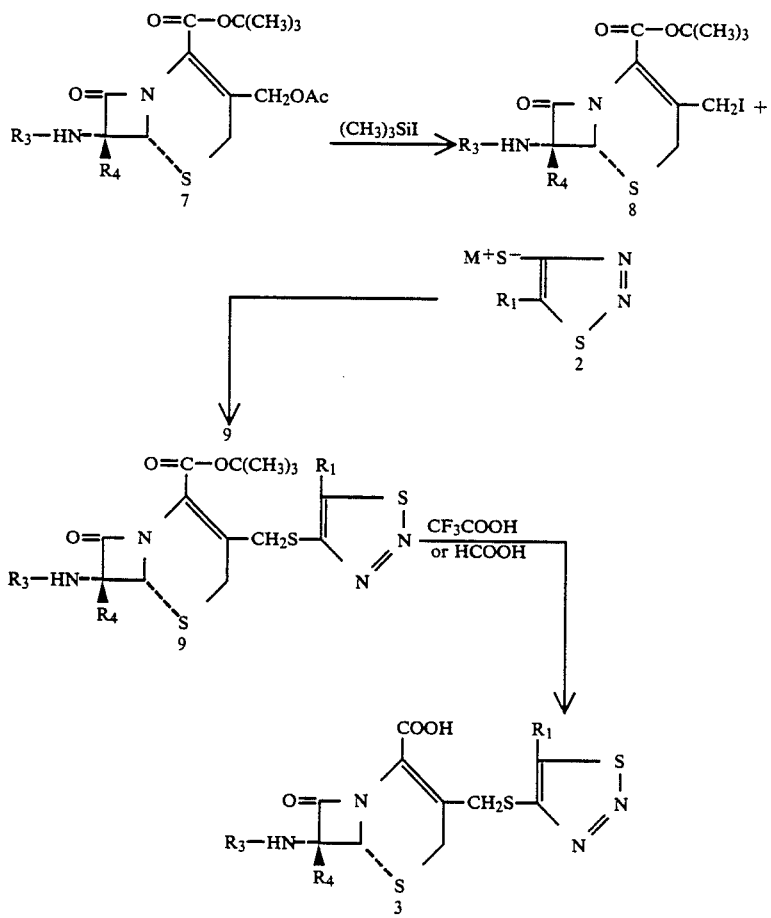

According to Scheme D a cephalosporin t-butyl ester 7 is reacted with trimethylsilyliodide giving 8 which is further reacted with a 1,2,3-thiadiazol-4-thiolate 2, giving 9 which is then deblocked producing cephalosporin derivatives 3.

Scheme E

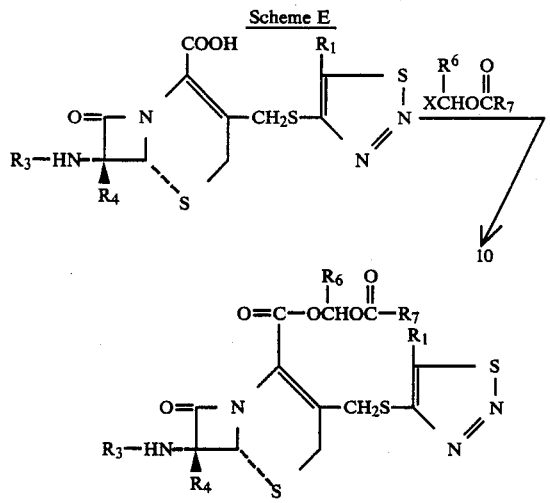

According to Scheme E, cephalosporin 3 is reacted with

where $R_6$ is alkyl and $R_7$ is alkyl or alkoxy or $R_6$ and $R_7$ are cycloalkyl and X is halogen, giving cephalosporins 10.

In the above schemes, the 1,2,3-thiadiazol-4-thiolates

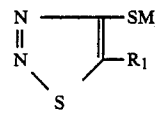

are the subject of a United States patent application by the same inventors, which was filed on the same date as the parent application of this instant application. The disclosure of such co-pending application, Ser. No. 883,189, now No. 4,803,280 is incorporated by reference.

The compounds of the present invention are active antibacterial agents as established in the in vitro agar dilution test using Mueller-Hinton agar. The test compounds were dissolved in a mixture of dimethyl sulfoxide and aqueous sodium bicarbonate and applied as 1 ml of drug solution plus 9 ml of agar per plate. The innoculum was a 5 hour TSB shake culture diluted to $10^{-2}$ with Mueller-Hinton broth and applied to the plates with a Steers' Replicator.

The results of this test on representative compounds of this invention (identified by Example Number) against a variety of microorganisms appear in Tables I and II in terms of minimal inhibitory concentration (MIC) in mcg/ml together with Cefotaxime, Cephalothin and Ampicillin as positive controls.

TABLE I

| Microorganism | | MIC (mcg/ml) | | | |
|---|---|---|---|---|---|
| | | Example No. 2 | Example No. 1 | Example No. 6 | Cefotaxime |
| Klebsiella | STFD 79-6 | .06 | .5 | 2 | ≦.015, .06 |
| Klebsiella | SSC 78-1 | .06 | .5 | 1 | ≦.015, .06 |
| Enterobacter aerogenes | STFD 79-14 | .5 | 1 | 4 | .03, .06 |
| Enterobacter cloacae | K 79-16 | 2 | 4 | 1 | .03, .25, .06 |
| Serratia | TUL 78-15 | 32 | 8 | 8 | 1, 2, .25 |
| Serratia | QHC 77-2 | 32 | 8 | 8 | .5, 1, .12 |
| Proteus morganii | K 79-25 | .5 | .5 | 16 | .25, ≦.015, ≦.06 |
| Proteus rettgheri | N 76-1 | ≦.03 | ≦.015 | — | ≦.015 |
| Proteus rettgheri | K 77-6 | — | — | ≦.12 | ≦.06 |
| Escherichia coli | STFD 79-20 | .25 | .5 | .5 | ≦.015, ≦.06 |
| Escherichia coli | 311 | .25 | .5 | .5 | ≦.015, ≦.06 |
| Salmonella | SSC 79-57 | 4 | 4 | 8 | .25 |
| Salmonella ariz. | QHC 77-3 | 1 | 1 | 2 | ≦.015, ≦.06 |
| Acinetobacter | STFD 79-17 | 128 | 16 | 32 | 8, 16 |
| Acinetobacter | K 77-1 | 16 | 4 | 32 | 4, 2, 8 |
| Pseudomonas | SSC 78-13 | >256 | 128 | 64 | 32 |
| Pseudomonas | 12-4-4 | >256 | >128 | 64 | 16, 8 |
| Enterococcus | OSU 75-1 | 256 | 128 | 256 | 128, 64, >128 |
| Enterococcus | SM 77-15 | 256 | 64 | 128 | 128, 32, 64 |
| Staphylococcus | SSC 79-18β− | 8 | 1 | 1 | 1, 2, .5 |
| Staphylococcus | FU 79-19-2β+ | 32 | 4 | 16 | 4, 8 |
| Escherichia coli | ESS 22-31 | ≦.03 | ≦.015 | .5 | ≦.015, ≦.06 |
| Klebsiella pneumoniae | AD | .06 | .25 | .25 | ≦.015, ≦.06 |
| Micrococcus lutea | PCI 1001 | .06 | — | .25 | ≦.015, .25 |
| Staphylococcus Smith | | 8 | 1 | 2 | 1, 2 |
| Pseudomonas aeruginosa | ATCC 27853 | >256 | 128 | 128 | 16, 32 |
| Escherichia coli | ATCC 25922 | .06 | .12 | 2 | ≦.015, ≦.06 |
| Staphylococcus | ATCC 25923 | 16 | 2 | 4 | 1, .25 |
| Providencia stuarti | SSC 80-78 | — | — | 5 | ≦.06 |
| Providencia stuarti | K 81-29 | — | — | 1 | .25 |

TABLE II

| Microorganism | | MIC (mcg/ml) | | | |
|---|---|---|---|---|---|
| | | Example No. 10 | Example No. 8 | Cephalothin | Ampicillin |
| Escherichia coli | ATCC 25922 | 64 | 64 | 16 | 4 |

TABLE II-continued

|  |  | MIC (mcg/ml) | | | |
|---|---|---|---|---|---|
| Microorganism | | Example No. 10 | Example No. 8 | Cephalothin | Ampicillin |
| Escherichia coli | CMC 84-11 | 128 | 64 | 8 | 4 |
| Escherichia coli | CMC 84-16 | 128 | 64 | 16 | >256 |
| Klebsiella pneumoniae | AD (MP) | 16 | 8 | 1 | .25 |
| Klebsiella pneumoniae | MOR 84-4 | 64 | 32 | 2 | 32 |
| Klebsiella oxytoca | MOR 84-28 | 128 | 256 | >256 | 32 |
| Enterobacter cloacae | VGH 84-37 | >256 | >256 | >256 | >256 |
| Enterobacter cloacae | K 84-10 | >256 | >256 | >256 | >256 |
| Enterobacter aerogenes | VGH 84-36 | >256 | 256 | >256 | 256 |
| Serratia marcesans | K 84-18 | >256 | >256 | >256 | 64 |
| Serratia marcesans | F 35 (MP) | >256 | >256 | >256 | >256 |
| Proteus rettgheri | CMC 84-41 | 4 | 2 | 4 | .5 |
| Morganella morganii | VGH 84-11 | >256 | >256 | >256 | >256 |
| Morganella morganii | CMC 84-37 | >256 | >256 | >256 | 256 |
| Pseudomonas aeruginosa | 12-4-4 (MP) | >256 | >256 | >256 | >256 |
| Pseudomonas aeruginosa | VGH 84-4 | >256 | >256 | >256 | >256 |
| Acinetobacter calcoaceticus | MOR 84-43 | >256 | >256 | >256 | 32 |
| Staphylococcus aureus | ATCC 25923 | .5 | .5 | .25 | ≦.12 |
| Staphylococcus aureus | Smith (MP) | ≦.12 | ≦.12 | ≦.12 | ≦.12 |
| Staphylococcus aureus | CMC 83-128 | 1 | 1 | ≦.12 | ≦.12 |
| Staphylococcus epidermidis | CMC 83-135 | ≦.12 | ≦.12 | ≦.12 | ≦.12 |
| Staphylococcus epidermidis | IO 83-58 | 2 | 2 | .25 | 16 |
| Staphylococcus saprophyticus | VGH 84-50 | 1 | 1 | .25 | ≦.12 |
| Enterococcus | VGH 84-65 | 32 | 32 | 32 | 1 |
| Escherichia coli | No. 311(Parent) | 64 | 32 | 8 | 2 |
| Escherichia coli | No. 311 N.A. | 64 | 32 | 8 | 2 |
| Staphylococcus aureus | CMC 83-131 | 32 | 32 | 32 | 2 |
| Staphylococcus aureus | CMC 83-132 | 32 | 32 | 32 | 1 |

EXAMPLE 1

(Z)-7-[[(2-Amino-4-thiazolyl)(methoxyimino)acetyl]amino]-8-oxo-3-[[(5-phenyl-1,2,3-thiadiazol-4-yl)thio]mehtyl]-5-thia-1-azabicyclo[4.2.0]oct-2-ene-2-carboxylic acid A mixture of 0.5 g of 3-[(acetyloxy)methyl]-7β-[[(2-amino-4-thiazolyl)(methoxyimino)acetyl]amino]-8-oxo-5-thia-1-azabicyclo[4.2.0]oct-2-ene-2-carboxylic acid, sodium salt (Cefotaxime, sodium salt), 0.4 g of 5-phenyl-1,2,3-thiadiazole-4-thiol, sodium salt and 10 ml of water was stirred and heated at 55°-60° C. for 5.5 hours with acid adjustment to pH 6.5 every hour. The mixture was then chilled overnight and filtered through diatomaceous earth. The filtrate was adjusted to pH 5 with dilute hydrochloric acid and then extracted twice with ethyl acetate. The aqueous remainder was filtered through diatomaceous earth, readjusted to pH 5 and added to a 50 ml column of Amberlite ® XAD-2 ion exchange resin. The column was washed with water, then with methanol. The methanolextract was evaporated, giving 150 mg of the desired product as a cream colored solid: IR(KBr) 1760 cm$^{-1}$ (β-lactam —C=O).

EXAMPLE 2

(Z)-7-[[(2-Amino-4-thiazolyl)(methoxyimino)acetyl]amino]-3-[[[5-[4-(1,1-dimethylethyl)phenyl]-1,2,3-thiadiazol-4-yl]thio]methyl]-8-oxo-5-thia-1-azabicyclo[4.2.0]oct-2-ene-2-carboxylic acid A mixture of 0.5 g of Cefotaxime, sodium salt, 0.4 g of 5-[4-(1,1-dimethylethyl)phenyl]-1,2,3-thiadiazole-4-thiol, potassium salt and 16 ml of water was heated at 70° C. for 5.5 hours with pH adjustment to 6.8-7.2, then cooled and filtered. The filtrate was adjusted to pH 5 and extracted with 30 ml of ethyl acetate. The aqueous remainder was filtered through diatomaceous earth and adjusted to pH 2.5 with 2N hydrochloric acid. The resulting solid was collected, washed with water and dried, giving 86 mg of the desired product as a light orange solid [α]$_D^{26}$= −10°+2 (0.885 DMSO): IR(KBr) 1770 cm$^{-1}$ (β-lactam —C=O).

EXAMPLE 3

7-Amino-3-[[[5-(1,1-dimethylethyl)-1,2,3-thiadiazol-4-yl]thio]methyl]-8-oxo-5-thia-1-azabicyclo[4.2.0]oct-2-ene-2-carboxylic acid A mixture of 3.55 g of 3-[(acetyloxy)methyl]-7β-amino-8-oxo-5-thia-1-azabicyclo[4.2.0]oct-2-ene-2-carboxylic acid (7-aminocephalosporanic acid), 2.55 g of 5-(1,1-dimethylethyl)-1,2,3-thiadiazole-4-thiol, sodium salt, 1.11 g of sodium bicarbonate, 65 ml of water and 30 ml of acetone was stirred at reflux for 2 hours, then cooled and filtered. The filtrate was treated with activated charcoal, then filtered through diatomaceous earth. This filtrate was acidified to pH 3.4 with 2N hydrochloric acid. The solid was collected, washed with water and dried, giving 1.5 g of the desired product as a beige solid: IR(KBr) 1780 cm$^{-1}$ (β-lactam —C=O).

EXAMPLE 4

7-Amino-3-[[[5-(1,1-dimethylethyl)-1,2,3-thiadiazol-4-yl]thio]-methyl]-8-oxo-5-thia-1-azabicyclo[4.2.0]oct-2-ene-2-carboxylic acid diphenylmethyl ester A mixture of 1.4g of 7β-amino-3-[[[5-(1,1-dimethylethyl)-1,2,3-thiadiazol-4-yl]thio]methyl]-8-oxo-5-thio-1-azabicyclo[4.2.0]oct-2-ene-2-carboxylic acid and 3.0 g of diphenyldiazomethane in 50 ml of acetonitrile was stirred for 48 hours, then filtered and the filtrate evaporated to an oil. This oil was purified by repeated chromatography on preparative TLC plates, eluting with ethyl acetate:hexane (1:2), giving 914 mg of the desired product as a beige solid: IR(KBr) 1775 cm$^{-1}$ (β-lactam —C=O).

EXAMPLE 5

(Z)-3-[[[5-(1,1-Dimethylethyl)-1,2,3-thiadiazol-4-yl]-thio]methyl]-7-[[(methoxyimino)[2-[(triphenylmethyl)amino]-4-thiazolyl]acetyl]amino]-8-oxo-5-thia-1-azabicyclo[4.2.0]oct-2-ene-2-carboxylic acid, diphenylmethyl ester A mixture of 444 mg of 2-(2-tritylaminothiazol-4-yl)-2-[Z]-methoximinoacetic acid, 553 mg of 7β-amino-3-[[[5-(1,1-dimethylethyl)-1,2,3-thiadiazol-4-yl]thio]methyl]-8-oxo-5-thia-1-azabicyclo[4.2.0]oct-2-ene-2-carboxylic acid, diphenylmethyl ester, 247 mg of 2-ethoxy-1(2H)-quinolinecarboxylic acid, ethyl ester and 15 ml of dichloromethane was stirred at room temperature overnight. The solution was extracted with 0.5N, hydrochloric acid, water, saturated aqueous sodium bicarbonate and brine, then evaporated, giving 808 mg of the desired product as a yellow glass: IR(KBr) 1785 cm$^{-1}$ (β-lactam —C=O).

EXAMPLE 6

(Z)-7-[[(2-Amino-4-thiazolyl)(methoxyimino)acetyl]amino]-3-[[[5-(1,1-dimethylethyl)-1,2,3-thiadiazol-4-yl]thio]methyl]-8-oxo-5-thia-1-azabicyclo[4.2.0]oct-2-ene-2-carboxylic acid A 750 mg portion of (Z)-3-[[[5-(1,1-dimethylethyl)-1,2,3-thiadiazol-4-yl]thio]methyl]-7β-[[(methoxyimino)[(triphenylmethyl)amino]-4-thiazolyl]acetyl]amino]-8-oxo-5-thia-1-azabicyclo[4.2.0]oct-2-ene-2-carboxylic acid, diphenylmethyl ester and 5 drops of anisole were dissolved in 10 ml of dichloromethane in an ice bath. A 2 ml portion of trifluoroacetic acid was added, the mixture was stirred for 3 hours at room temperture, then evaporated at reduced pressure and triturated with ether. The resulting solid was collected, washed with ether, dried in vacuo and then stirred with 5 ml of 80% formic acid for 2 hours. The mixture was diluted with 5 ml of water and filtered. The filtrate was treated with activated charcoal, refiltered and evaporated to dryness. The residue was triturated with ether giving 260 mg of the desired product as a solid: IR(KBr) 1770 cm$^{-1}$ (β-lactam —C=O).

EXAMPLE 7

(6R-trans)-3-[[(5-Methyl-1,2,3-thiadiazol-4-yl)thio]methyl]-8-oxo-7-[(2-thienylacetyl)amino]-5-thia-1-azabicyclo[4.2.0]oct-2-ene-2-carboxylic acid, 1,1-dimethylethyl ester A solution of 2.60 g of t-butyl 7β-(thienylacetylamino)-3-iodomethyl-8-oxo-5-thia-1-azabicyclo[4.2.0]oct-2-ene-2-carboxylate, 800 mg of 5-methyl-1,2,3-thiadiazole-4-thiol, sodium salt and 75 ml of dry ethanol was stirred for 2 hours. The solvent was evaporated in vacuo, the residue taken up in dichloromethane, filtered and then chromatographed over Bio-Sil A (40×400 mm) eluting with a gradient of 0% to 2% methanol in dichloromethane. The desired fractions were combined, evaporated and crystallized from ethanol, giving 1.75 g of the desired compound, mp 155°–157° C. $^1$H NMR (300 MHz, CDCl$_3$): δ 1.49 (s, 9H, t-butyl); 2.57 (s, 3H, CH$_3$); 3.65 (AB quartet, 2H, 4-CH$_2$); 3.85 (s, 2H, CH$_2$CO); 4.18 (AB quartet, 2H, CH$_2$S); 4.93 (d, 1H, J=4.9 Hz, 6-H); 5.80 (dd, 1H, J=9.2 Hz, 4.9 Hz, 7-H); [6.97 (m, 2H) and 7.26 (m, 1H)(thienyl)].

EXAMPLE 8

(6R-trans)-3-[[(5-Methyl-1,2,3-thiadiazol-4-yl)thio]methyl]-8-oxo-7-[(2-thienylacetyl)amino]-5-thia-1-azabicyclo[4.2.0]oct-2-ene-2-carboxylic acid A cold (0° C.) solution of 2.62 g of the product of Example 7 in 20 ml of dry anisole and 25 ml of dichloromethane was treated with 20 ml of trifluoroacetic acid. After evaporation the residue was chromatographed as described in Example 7, giving 950 mg of the desired product. $^1$H NMR (300 MHz, CDCl$_3$): δ 2.57 (s, 3H); 3.70 (AB quartet, 2H, 4-CH$_2$); 3.87 (s, 2H); 4.17 (AB quartet, 2H, CH$_2$S—); 4.97 (d, 1H, J=4.8 Hz, 6-H); 5.76 (dd, 1H, J=9.24 Hz, 4.8 Hz, 7-H); [6.98 (m, 2H) and 7.24 (m, 1H)(thienyl)].

EXAMPLE 9

(6R-trans)-3-[[(5-Ethyl-1,2,3-thiadiazol-4-yl)thio]methyl]-8-oxo-7-[(2-thienylacetyl)amino]-5-thia-1-azabicyclo[4.2.0]oct-2-ene-2-carboxylic acid, 1,1-dimethylethyl ester A solution of 2.62 g of 7β-(thienylacetylamino)-3-iodomethyl-8-oxo-5-thia-1-azabicyclo[4.2.0]oct-2-ene-2-carboxylic acid, 1,1-dimethylethyl ester, 900 mg of 5-ethyl-1,2,3-thiadiazo-4-ylthiol, sodium salt and 75 ml of dry ethanol was stirred for 2 hours, then the solvent was removed in vacuo. The residue was taken up in dichloromethane, filtered and chromatographed on Bio-Sil A (40×400 mm), eluting with a 0% to 2% gradient of methanol in dichloromethane. The desired fractions were combined and crystallized from ethyl acetate-hexane, giving 2.3 g of the desired compound, mp 167.5°–169° C. $^1$H NMR (300 MHz, CDCl$_3$): δ 1.35 (t, 3H); 1.56 (s, 9H); 2.95 (q, 2H); 3.65 (AB quartet, 2H, 4-CH$_2$); 3.85 (s, 2H); 4.18 (AB quartet, 2H, CH$_2$S); 4.93 (d, 1H, J=4.9 Hz, 6-H); 5.80 (dd, 1H, J=9.2 Hz, 4.9 Hz, 7-H; [6.98 (m, 2H) and 7.26 (m, 1H) (thienyl)].

EXAMPLE 10

(6R-trans)-3-[[(5-Ethyl-1,2,3-thiadiazol-4-yl)thio]methyl]-8-oxo-7-[(2-thienylacetyl)amino]-5-thia-1-azabicyclo[4.2.0]oct-2-ene-2-carboxylic acid A cold (0° C.) solution of 1.08 g of the product of Example 9 in 5 ml of dry anisole and 25 ml of dichloromethane was treated with 10 ml of trifluoroacetic acid. After 30 minutes the solvents were removed in vacuo and the crude acid was dissolved in ethyl acetate and extracted twice with 5% aqueous sodium bicarbonate. The alkaline extracts were combined, acidified to pH 3 and extracted three times with ethyl acetate. These extracts were combined, dried and concentrated in vacuo giving a light orange foam. This foam was suspended in diethyl ether and collected, giving 650 mg of the desired product. $^1$H NMR (300 MHz, CDCl$_3$): δ 1.32 (t, 3H); 2.95 (q, 2H); 3.68 (AB quartet, 2H, 4-CH$_2$); 3.86 (s, 2H); 4.19 (AB quartet, 2H, CH$_2$S); 4.98 (d, 1H, J=4.8 Hz, 6-H); 5.79 (dd, 1H, J=9.2 Hz, 4.8 Hz, 7-H); [6.98 (m, 2H) and 7.25 (m, 1H)(thienyl)].

EXAMPLE 11

(6R-trans)-7-[[[(2-Triphenylmethylamino)-4-thiazolyl]-(methoxyimino)acetyl]amino]-3-[[(5-methyl-1,2,3-thiadiazol-4-yl)thio]methyl]-8-oxo-5-thia-1-azabicyclo[4.2.0]oct-2-ene-2-carboxylic acid, 1,1-dimethylethyl ester A solution of 2.06 g of (Z)-7β-[[[(2-triphenylmethylamino)-4-thiazolyl](methoxyimino)acetyl]amino]-3-iodomethyl-8-oxo-5-thia-1-azabicyclo[4.2.0]oct-2-ene-2-carboxylic acid, 750 mg of 5-methyl-1,2,3-thiadiazole-4-thiol, sodium salt and 50 ml of ethanol was stirred for one hour and then concentrated in vacuo. The oily residue was taken up in dichloromethane, filtered and chromatographed over a Bio-Sil A column (40×400 mm), eluting with a gradient of 0% to 5% methanol in dichloromethane. The desired fractions were combined, concentrated in vacuo to give an orange foam which was triturated with hexane and the amorphous solid collected, giving 1.1 g of the desired product. 'H NMR (300 MHz, CDCl$_3$): δ 1.50 (s, 9H); 2.58 (s, 3H); 3.70 (AB quartet, 2H, 4-H); 4.07 (s, 3H); 4.19 (AB quartet, 2H, (CH$_2$S); 5.02 (d, 1H, J=4.9 Hz, 6-H); 5.93 (dd, 1H, J=9.2 Hz, 4.9 Hz, 7-H); 6.73 (s, 1H, thiazole H); 6.85 (d, NH); 7.29 (bs, 15H).

EXAMPLE 12

[6R-[6α,7β(Z)]]-7-[[(2-Amino-4-thiazolyl(methoxyimino)acetyl]amino]-3-[[(5-methyl-1,2,3-thiadiazol-4-yl)thio]methyl]-8-oxo-5-thia-1-azabicyclo[4.2.0]oct-2-ene-2-carboxylic acid A cold (0° C.) solution of 840 mg of the product of Example 11 in 2 ml of anisole and 10 ml of dry dichloromethane was treated with 5 ml of trifluoroacetic acid. After 30 minutes the solvents were removed in vacuo and the crude acid triturated with diethyl ether. The resulting crude acid was dissolved in an excess of 5% aqueous sodium bicarbonate, filtered and reacidified to pH 3. The resulting orange precipitate was collected, washed with water and dried in vacuo giving the desired product. 'H NMR (300 MHz, CD$_3$SOCD$_3$): δ 2.45 (s, 3H); 3.55 (AB quartet, 2H, 4-H); 3.85 (s, 3H); 4.20 (AB quartet, 2H, CH$_2$S); 5.05 (d, 1H, J=4.9Hz, 6-H); 5.65 (dd, 1H, J=9.2Hz, 4.9 Hz, 7-H); 6.75 (s, 1H, thiazole H); 7.21 (bs, NH$_2$); 9.60 (d, NH). Infrared absorption (MBr pellet) 1770 cm$^{-1}$.

EXAMPLE 13

(6R-trans)-7-[[[(2-Triphenylmethylamino)-4-thiazolyl]-(methoxyimino)acetyl]amino]-3-[[[5-ethyl-1,2,3-thiadiazol-4-yl]thio]methyl]-8-oxo-5-thia-1-azabicyclo[4.2.0]oct-2-ene-2-carboxylic acid, 1,1-dimethylethyl ester A solution of 7.0 g of 7β-[[[(2-triphenylmethylamino)-4-thiazolyl](methoxyimino)acetyl]amino]-3-iodomethyl-8-oxo-5-thia-1-azabicyclo[4.2.0]oct-2-ene-2-carboxylic acid, 1,1-dimethylethyl ester, 1.68 g of 5-ethyl-1,2,3-thiadiazole-4-thiol, sodium salt and 100 ml of dry ethanol was stirred for 2 hours and then concentrated in vacuo. The residue was takenup in 75 ml of dichloromethane, applied to a 60×560 mm column of Bio-Sil A and eluted with a gradient of 0% to 5% methanol in dichloromethane. The desired fractions were combined and concentrated in vacuo, giving 4.5 g of the desired compound as a light yellow foam. 'H NMR (300 MHz, CDCl$_3$): δ 1.34 (t, 3H); 1.55 (s, 9H); 2.94 (q, 2H); 3.70 (AB quartet, 2H-4H); 4.06 (s, 3H); 4.18 (AB quartet, 2H, CH$_2$S); 5.02 (d, 1H, J=4.8 Hz, 6-H); 5.91 (dd, 1H, J=9.2 Hz, 4.8 Hz, 7-H); 6.75 (s, 1H, thiazole H); 6.81 (d, NH); 7.28 (bs, 15H).

EXAMPLE 14

[6R-[6α,7β(Z)]]-7-[[(2-Amino-4-thiazolyl)(methoxyimino)acetyl]amino]-3-[[(5-ethyl-1,2,3-thiadiazol-4-yl)thio]methyl]-8-oxo-5-thia-1-azabicyclo[4.2.0]oct-2-ene-2-carboxylic acid The produce of Example 12 was repeated using the product of Example 13, giving the desired product. 'H NMR (300 MHz, CD$_3$SOCD$_3$): δ 1.30 (t, 3H); 2.90 (q, 2H); 3.55 (AB quartet, 2H, 4-H); 3.86 (s, 3H); 4.16 (AB quartet, 2H, CH$_2$S); 5.03 (d, 1H, J=4.8 Hz, 6-H); 5.71 (dd, 1H, J=9.2 Hz, 4.8 Hz, 7-H); 6.76 (s, 1H, thiazole H) 7.20 (bs, NH$_2$); 9.60 (d, NH).

EXAMPLE 15

(Z)-7-[[(2-Amino-4-thiazolyl)(methoxyimino)acetyl]amino]-3-[[[5-ethyl-1,2,3-thiadiazol-4-yl]thio]methyl]-8-oxo-5-thia-1-azabicyclo[4.2.0]oct-2-ene-2-carboxylic acid, acetoxymethyl ester A cold (0° C.) solution of 200 mg of (Z)-7β-[[(2-amino-4-thiazolyl)(methoxyimino)acetyl]amino]-3-[[[5-ethyl-1,2,3-thiadiazol-4-yl]thio]methyl]-8-oxo-5-thia-1-azabicyclo[4.2.0]oct-2-ene-2-carboxylic acid, sodium salt in 10 ml of dry dimethylformamide was treated with 200 mg of iodomethyl acetate. After 2 hours at 0° C. the mixture was diluted with ice water and extracted with ethyl acetate. The organic extract was dried and concentrated in vacuo to a foam which was taken up in dichloromethane and chromatographed over a Bio-Sil A column, eluting with a gradient of 0% to 5% methanol in dichloromethane. The desired fractions were concentrated giving a foam which was triturated with ether, giving 50 mg of the desired ester. Infrared spectrum (KBr pellet) 1775 cm$^{-1}$.

EXAMPLE 16

(Z)-7-[[(2-Amino-4-thiazolyl)(methoxyimino)acetyl]amino]-3-[[[5-ethyl-1,2,3-thiadiazol-4-yl]thio]methyl]-8-oxo-5-thia-1-azabicyclo[4.2.0]oct-2-ene-2-carboxylic acid, ethoxycarbonylethoxy ester The procedure of Example 15 is repeated using α-iodoethyl ethyl carbonate instead of iodomethyl acetate, giving the desired compound.

We claim:

1. A compound having the formula:

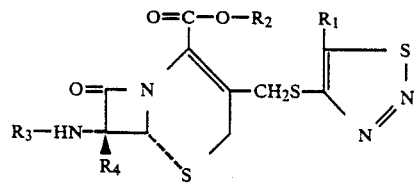

wherein R$_1$ is selected from the group consisting of hydrogen, alkyl(C$_1$-C$_6$), phenyl and substituted phenyl wherein the substituents are alkyl(C$_1$-C$_6$); R$_2$ is selected from the group consisting of hydrogen, diphenylmethyl, α-acyloxyalkyl, t-butyl, benzyl, 4-nitrobenzyl and 4-methoxybenzyl and pharmaceutically acceptable salts selected from the group consisting of sodium and potassium; and R$_3$ is selected from the group consisting of

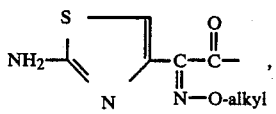

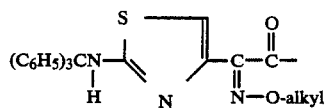

and 2-thienylacetyl; and $R_4$ is selected from the group consisting of hydrogen, —O—alkyl, —S—alkyl and formamido.

2. The compound according to claim 1, (Z)-7-[[(2-amino-4-thiazolyl)(methoxyimino)acetyl]amino]-8-oxo-3-[[(5-phenyl-1,2,3-thiadiazol-4-yl)thio]methyl]-5-thia-1-azabicyclo[4.2.0]oct-2-ene-2-carboxylic acid.

3. The compound according to claim 1, (Z)-7-[[(2-amino-4-thiazolyl)(methoxyimino)acetyl]amino]-3-[[[5-[4-(1,1-dimethylethyl)phenyl]-1,2,3-thiadiazol-4-yl]thio]methyl]-8-oxo-5-thia-1-azabicyclo[4.2.0]oct-2-ene-2-carboxylic acid.

4. The compound according to claim 1, (Z)-3-[[[5-(1,1-dimethylethyl)-1,2,3-thiadiazol-4-yl]thio]methyl]-7-[[(methoxyimino)[2-[(triphenylmethyl)amino]-4-thiazolyl]acetyl]amino]-8-oxo-5-thia-1-azabicyclo[4.2.0]-oct-2-ene-2-carboxylic acid, diphenylmethyl ester.

5. The compound according to claim 1, (Z)-7-[[(2-amino-4-thiazolyl)(methoxyimino)acetyl]amino]-3-[[[5-(1,1-dimethylethyl)-1,2,3-thiadiazol-4-yl]thio]methyl]-8-oxo-5-thia-1-azabicyclo[4.2.0]-oct-2-ene-2-carboxylic acid.

6. The compound according to claim 1, (6R-trans)-3-[[(5-methyl-1,2,3-thiadiazol-4-yl)thio]methyl]-8-oxo-7-[(2-thienylacetyl)amino]-5-thia-1-azabicyclo[4.2.0]oct-2-ene-2-carboxylic acid, 1,1-dimethylethyl ester.

7. The compound according to claim 1, (6R-trans)-3-[[(5-methyl-1,2,3-thiadiazol-4-yl)thio]methyl]-8-oxo-7-[(2-thienylacetyl)amino]-5-thia-1-azabicyclo[4.2.0]oct-2-ene-2-carboxylic acid.

8. The compound according to claim 1, (6R-trans)-3-[[(5-ethyl-1,2,3-thiadiazol-4-yl)thio]methyl]-8-oxo-7-[(2-thienylacetyl)amino]-5-thia-1-azabicyclo-[4.2.0]oct-2-ene-2-carboxylic acid, 1,1-dimethylethyl ester.

9. The compound according to claim 1, (6R-trans)-3-[[(5-ethyl-1,2,3-thiadiazol-4-yl)thio]methyl]-8-oxo-7-[(2-thienylacetyl)amino]-5-thia-1-azabicyclo[4.2.0]oct-2-ene-2-carboxylic acid.

10. The compound according to claim 1, (6R-trans)-7-[[[(2-triphenylmethylamino)-4-thiazolyl](methoxyimino)acetyl]amino]-3-[[(5-methyl-1,2,3-thiadiazol-4-yl)thio]methyl]-8-oxo-5-thia-1-azabicyclo[4.2.0]oct-2-ene-2-carboxylic acid, 1,1-dimethylethyl ester.

11. The compound according to claim 1, [6R-[6α,7β(Z)]]-7-[[(2-amino-4-thiazolyl(methoxyimino)acetyl]amino]-3-[[(5-methyl-1,2,3-thiadiazol-4-yl)thio]methyl]-8-oxo-5-thia-1-azabicyclo[4.2.0]oct-2-ene-2-carboxylic acid.

12. The compound according to claim 1, (6R-trans)-7-[[[(2-triphenylmethylamino)-4-thiazolyl](methoxyimino)acetyl]amino]-3-[[[5-ethyl-1,2,3-thiadiazol-4-yl]thio]methyl]-8-oxo-5-thia-1-azabicyclo[4.2.0]oct-2-ene-2-carboxylic acid, 1,1-dimethylethyl ester.

13. The compound according to claim 1, [6R-[6α,7β(Z)]]-7-[[(2-amino-4-thiazolyl)(methoxyimino)acetyl]amino]-3-[[(5-ethyl-1,2,3-thiadiazol-4-yl)thio]methyl]-8-oxo-5-thia-1-azabicyclo[4.2.0]oct-2-ene-2-carboxylic acid.

14. The compound according to claim 1, (Z)-7-[[(2-amino-4-thiazolyl)methoxyimino)acetyl]amino]-3-[[[5-ethyl-1,2,3-thiadiazol-4-yl]thio]methyl]-8-oxo-5-thia-1-azabicyclo[4.2.0]oct-2-ene-2-carboxylic acid, acetoxymethyl ester.

15. The compound according to claim 1, (Z)-7-[[(2-amino-4-thiazolyl)(methoxyimino)acetyl]amino]-3-[[[5-ethyl-1,2,3-thiadiazol-4-yl]thio]methyl]-8-oxo-5-thia-1-azabicyclo[4.2.0]oct-2-ene-2-carboxylic acid, ethoxycarbonylethoxy ester.

16. The compound of claim 1, wherein $R_1$ is hydrogen.

17. The compound of claim 1, wherein $R_1$ is methyl.

18. The compound of claim 1, wherein $R_1$ is ethyl.

19. The compound of claim 1, wherein $R_1$ is n-propyl.

20. The compound of claim 1, wherein $R_1$ is isopropyl.

21. The compound of claim 1, wherein $R_1$ is n-butyl.

* * * * *